United States Patent [19]

Safford, Jr.

[11] 4,195,074

[45] Mar. 25, 1980

[54] PROCESS FOR PRODUCING A SOLUBLE RUBELLA ANTIGEN

[75] Inventor: John W. Safford, Jr., Wauconda, Ill.

[73] Assignee: Abbott Laboratories, North Chicago, Ill.

[21] Appl. No.: 873,940

[22] Filed: Jan. 31, 1978

Related U.S. Application Data

[62] Division of Ser. No. 773,231, Mar. 1, 1977.

[51] Int. Cl.² .................. C12K 1/04; C12K 7/00; G01N 33/16; A61K 39/20
[52] U.S. Cl. ..................... 424/12; 260/112 R; 260/112 B; 424/8; 424/86; 424/89; 435/7; 435/239
[58] Field of Search ............ 424/12, 85, 86, 89, 424/93; 195/1.5, 1.7; 260/112 R, 112 B

[56] References Cited

PUBLICATIONS

Lowe, Affinity Chromatography, John Wiley & Sons, NY, 1974, pp. 44–56, 150–156, 165–166.
Salmi, Acta Path. & Micro Scand. Sect. B, Microbiol., vol. 80, No. 4, 1972, pp. 545–558.
Hassan, PSEBM, vol. 125, 1967, pp. 430–435.
LeBouvier, Nature, vol. 221, Jan. 4, 1969, pp. 78–79.
Salmi, Chem. Abs., vol. 78, 1973, Ab. No. 14295x.
Desyatskova, Chem. Abs., vol. 78, 1973, Ab. No. 70122a.
Chappel, The J. of Exptl. Med., vol. 139, 1974, pp. 497–511.
Schmidt, PSEBM, vol. 123, 1966, pp. 758–762.
Liebhaber, Virology, vol. 47, 1972, pp. 684–693.
Safford & Whittington, Fed. Proceedings, vol. 35, No. 3, Mar. 1, 1976, Ab. No. 3351, p. 813.

*Primary Examiner*—Anna P. Fagelson
*Attorney, Agent, or Firm*—Merriam, Marshall & Bicknell

[57] ABSTRACT

Purified soluble antigen, specific for rubella virus, is isolated from growth media of rubella-infected cell cultures by affinity and gel permeation chromatography and characterized, inter alia, by its specific activity. Antigen-sensitized particles are employed as immunoassay reagents in, for example, agglutination assays for detection and quantification of rubella antibodies in body fluids such as serum, spinal fluid and the like.

2 Claims, No Drawings

PROCESS FOR PRODUCING A SOLUBLE RUBELLA ANTIGEN

This is a division of application Ser. No. 773,231, filed Mar. 1, 1977.

BACKGROUND OF THE INVENTION

The present invention relates generally to materials and methods useful in the detection of antibodies and particularly relates to a novel, soluble, rubella virus antigen. The antigen of the invention is employed to develop specific immunoassay reagents useful for rapid detection and quantification of rubella antibodies in test fluids. Materials and methods of the present invention are useful in establishing the immunological status of a patient, (e.g., a woman of child-bearing age) and are also of value in diagnostic programs.

Procedures commonly employed for determination of anti-rubella antibodies in test fluids are based upon antibody inhibition of baby chick erythrocyte hemagglutination by an insoluble rubella virus particle. Among the essential steps of such procedures is the absorption of test fluids with kaolin to effect removal of non-specific lipoprotein inhibitors and absorption of the sera with baby chick erythrocytes to remove cross-reacting antibodies present in the fluid all prior to testing agglutination inhibition. Hemagglutination inhibition (HAI) assays of this type are relatively reliable but are time consuming because of the above-mentioned serum pre-treatment steps. Final test results are ordinarily not available for at least about 5–7 hours after test fluid collection. Other techniques for detection of antibody to rubella are summarized, e.g., in Meyer, H. M., et al., *Am. J. Chin. Pathol.*, 57: 803–813 (1972).

Prior attempts have been made to secure a soluble rubella virus antigen, apart from the insoluble hemagglutinins used in HAI tests. The art describes identification of two major "soluble" antigens (designated theta and iota) but attempts to definitively isolate and characterize these antigens from rubella-infected cell cultures have met with limited success and no soluble antigen heretofore isolated has been useful in developing an antigen-sensitized particle effective in detection and quantification of antibodies to rubella.

SUMMARY OF THE INVENTION

According to the present invention a soluble rubella virus antigen is isolated from media supporting growth of tissue culture cells infected with rubella virus. The antigen has a molecular weight of from about 40,000 to about 60,000 daltons; is insoluble in 50% saturated ammonium sulfate; and exhibits $\beta$ mobility in immunoelectrophoresis.

More specifically, the novel antigen is characterized by forming a single line precipitate with human serum reactive to rubella virus (as shown by hemagglutination inhibition tests). The antigen is further characterized as having a specific rubella antigen activity (S.R.A.A.) of from about 500 to about 10,000.

The purified antigen is isolated by process steps including: affinity chromatography; gel permeation chromatography; and isolation on the basis of relative reverse passive hemagglutination (RPHA) activity.

Immunological reagents of the invention are provided when the antigen is employed to sensitize immunologically inert particulate materials such as stabilized erythrocytes, bentonite, collodium, cholesterol crystals, quartz, synthetic resins, various kinds of synthetic latex, and liposomes prepared from phospholipids and sterols. Sensitized particles are employed in direct agglutination assays wherein rubella antibodies present in a given test fluid sample are rapidly detected by observation of particle agglutination phenomena and quantified by standard dilution techniques. This passive agglutination method does not ordinarily require removal from test fluid of non-specific inhibitors or antierythrocyte antibodies as do the HAI methods of the prior art.

Sensitized particles of the invention may also be employed in radioimmunoassay (RIA) and enzyme immunoassay (EIA) techniques. Further, the soluble antigen of the invention is expected to be useful in practice of well known immunoprecipitation assay technique.

Advantages attending the use of the antigen and reagents and practice of immunological assay methods of the invention will be apparent upon consideration of the following detailed description.

DETAILED DESCRIPTION

The soluble antigen of the invention is isolated from the culture medium of rubella virus infected cells. Cell lines suitable for tissue culture growth to obtain the antigen may include Baby Hamster Kidney (BHK-21), Porcine Stabile Kidney (PS), Serum Institute Rabbit Cornea (SIRC) and others well known in the art. In general, tissue cultures employed [according to the methods of Stewart, et al., *N.E. Jour. Med.* 276, No. 10 pp. 554–7(1967)] for production of insoluble rubella hemagglutinins for HAI tests are well suited for use according to this invention.

Isolation of the antigen proceeds by two-step chromatographic separation of growth medium components. As previously noted, the culture medium, preferably first concentrated by forced dialysis, is initially subjected to affinity chromatographic separation by passage through a column consisting of a solid phase to which IgG, derived from human serum known to contain antibodies reactive with rubella virus, has been conjugated or covalently bonded. Preferred solid phase materials for the column include agarose beads.

After washing through unbound material, the antigen bound to the IgG is eluted with a suitable buffer. A glycine-sodium hydroxide buffer with a pH in excess of 8 is preferred. Where particularly high pH buffers are employed, neutralization of eluted materials may be advisable.

Separation of the antigen from higher molecular weight material which may bind to the affinity column and be eluted with the buffer is accomplished by gel permeation chromatography involving, e.g., a Sephadex G-150 column. The effluent from the column is monitored on a UV spectrophotometer at 280 nm and reverse passive hemagglutination by standard techniques is employed to identify fractions containing the purified antigen. The agglutination employs, e.g., erythroctyes sensitized with human IgG from the same source as employed for preparing the affinity column.

The antigen so obtained is insoluble in 50 percent ammonium sulfate; displays a sedimentation coefficient of approximately 3.4S; has an estimated molecular weight of about 40,000 to 60,000 as determined by Sephadex G-150 chromatography; and exhibits $\beta$ mobility in immunoelectrophoresis.

The antigen is more particularly characterized by forming a single line precipitate with human serum reactive to rubella virus in hemagglutination inhibition tests. The antigen is also precisely characterized by having a specific rubella antigen activity (S.R.A.A.) of from about 500 to about 10,000. As employed herein, S.R.A.A. values are developed according to the following criteria. Any given crude tissue culture medium from growth of rubella-infected cells will display absorbancy at 280 nm. A typical crude medium from infected BHK-21 cells displays an absorbancy of about 1.1 when compared to water. The crude medium will also have a relatively fixed titer as determined by RPHA. Once again, a typical crude medium from infected BHK-21 cells will display a titer of 1:32. The "total $A_{280}$ units" of material found in the crude culture medium is defined as the volume (in ml) multiplied by the absorbance at 280 nm. By dividing the reciprocal of the RPHA titer by the total $A_{280}$ units, the S.R.A.A. is determined. S.R.A.A., therefore, equals the reciprocal of the RPHA titer divided by the total $A_{280}$ units.

The following illustrative examples relate to: (1) preparation of a "concentrated" cell culture medium containing the antigen of the invention; (2) preparation of human IgG for use in affinity chromatography and reverse passive hemagglutination; (3) preparation of the affinity gel; (4) preparation of the gel permeation chromatography column; (5) purification of the antigen from the "concentrated" medium; (6) preparation of rubella antigen-sensitized erythrocytes.

EXAMPLE I

Preparation of Concentrated Medium Containing Antigen

BHK-21 cells were monolayered in 20 liter roller bottles and innoculated with Gilchrist strain rubella virus. After three to four days of incubation, the medium was harvested and subjected to zonal centrifugation and effluent is saved. This effluent is concentrated 100-fold at 2°–8° C. in an Amicon DC-2 hollow fiber dialyzer concentrator. The concentrated material is clarified by centrifugation at 9000 rpm for 30 minutes followed by ultracentrifugation at 29000 rpm for 6 to 18 hours. The resulting concentrated material may be stored at −20° C.

EXAMPLE II

Preparation of IgG

Human recalcified plasma with a rubella titer of approximately 1:640 is precipitated with ammonium sulfate, dialyzed and purified according to the following procedural sequence.

(1) Equal 150 ml volumes of saturated ammonium sulfate and human recalcified plasma which is rubella positive are admixed at a rate of 6 to 10 ml/mixture while stirring with a magnetic stirrer at room temperature. The pH is adjusted to approximately 7.3 with sodium hydroxide.

(2) The mixture is stirred for approximately one hour and the precipitate form is collected by centrifugation at 9000 rpm for 30 minutes at 2°-8° C.

(3) Centrifuged precipitate is added to dialysis tubing and dialyzed against two liters of 0.01 M $K_2HPO_4$/0.01 M $KH_2PO_4$ buffer, pH of 8.0, with five changes of two liters each of the same buffer over 48 hours.

(4) The dialyzed material is recovered and is further purified through use of a Whatman DE52 Diethylaminoethyl Cellulose Microgranular (preswollen) Anion Exchanger and the IgG pool collected is subjected to further concentration, clarified by centrifugation and stored.

(6) The final yield of IgG recovered ranges from 150 mg to 160 mg per 70 ml of whole serum.

EXAMPLE III

Preparation of Affinity Gel

Sepharose 4b (Pharmacia) or any suitable agarose solid phase is activated with cyanogen bromide, 97% (Aldrich) in acetonitrile and subsequently coupled with human IgG (as prepared in Example II). The coupling of IgG to the solid phase is accomplished by practice of the method of Cuatrecasas, *J. Biol. Chem.*, 245: 3059–65 (1970) as modified in March, S.C., et al., *Analyt. Biochem.*, 60: 149–52 (1974).

EXAMPLE IV

Preparation of Gel Permeation Column

The gel permeation column for use in purifying antigen eluted from the affinity column is prepared by the following procedure.

(1) Eighteen gm of Sephadex G-150 (Pharmacia) is added to 1 liter of 0.05 M Tris-HCl in 0.15 M NaCl/0.02%$NaN_3$ pH 8.0 buffer, mixed, allowed to swell at room temperature for 3 days and degassed.

(2) The swollen gel slurry is added to a column to which the buffer has been added and partially drained, with hydrostatic pressure at 3–5 cm during the packing.

(3) The column is operated with use of a peristaltic pump, equilibrated with two bed volumes of the buffer at a flow rate of 4.8 $ml/cm^2$/hour, and tested for homogeneity with 6–8 ml of 0.2% Blue Dextran 2000, collecting 12 ml fractions.

EXAMPLE V

Purification of Antigen from Concentrated Medium

Purification of soluble antigen from the concentrate of Example I proceeds by (A) affinity chromatography and (B) gel permeation chromatography as follows:

A. Affinity Chromatography (1) The affinity column of Example III is warmed to room temperature and the buffer is drained to the top of the bed.

(2) The column is loaded with 3 bed volumes of ultracentrifuged "concentrate" of Example I at about 1 ml/minute flow rate.

(3) The column is washed with 5 bed volumes of 0.05 M Tris-HCl in 0.15 M NaCl-0.02% $NaN_3$ pH 8.0 buffer at 2–3 ml/minute.

(4) Following the wash, the column is eluted with 6 bed volumes of 0.1 M glycine-NaOH in 0.15 M NaCl pH 12 buffer at about 1 ml/minute. The eluted material is collected.

(5) With minimal delay, the eluted material is neutralized to pH 8.0 by adding 1 N HCl, dropwise, with constant stirring.

(6) The neutralized material is concentrated 5-fold of the original load volume in a single hollow fiber concentrator and clarified by centrifugation.

B. Gel Permeation Chromatography

The material eluted from the affinity column is chromatographed on a Sephadex G-150 column as prepared in Example IV. The fractions eluting in a volume expected to contain material with a molecular weight of 40,000 to 60,000 daltons are collected and RPHA titers are determined. Fractions with a titer equal to or in excess of 1:6400 are pooled. S.R.A.A. values may be determined based on the $A_{280}$ value and RPHA titer of the pooled fractions. Typically, the antigen is concentrated to a 3 to 8 ml volume from an original 80 to 100 liter volume of crude growth medium and has a S.R.A.A. value of from 500 to 10,000.

EXAMPLE VI

Rubella Antigen-Sensitized Erythrocytes

Human erythrocytes are stabilized according to the procedures disclosed in U.S. Pat. Nos. 3,714,345, 3,715,427 and/or 3,925,541; made up in 2.0 ml, 10% suspensions, and centrifuged for 2 to 3 minutes at 500–1000 rpm. The buffer is decanted and the cells are resuspended in 2.0 ml of 0.01 M acetate-pH 4.0 buffer. 0.2 ml of aqueous chromic chloride solution (10 mg $CrCl.6H_2O$/ml) is added to the erythrocyte suspension. 0.05 to 0.50 ml of antigen from Example 5 is added to the erythrocytes, the suspension is incubated at 30°–32° C. for 2 hours with mixing at 30 minute intervals. Sensitized erythrocytes are pelleted by centrifugation and the supernatant is discarded. The erythrocytes are washed twice by re-suspending in 0.1 M phosphate buffer and centrifuging as before. The pellet is re-suspended in 0.1 M phosphate buffer in quantities providing a 0.125% (v/v) suspension of sensitized erythrocytes.

EXAMPLE VII

Sensitized erythrocytes, essentially according to Example VI, were employed to determine the antibody titers of random human blood donor serum samples and results were compared to titers obtained by HAI techniques. 1336 serum samples were tested and the correlation coefficient (r) was determined as 0.99 by linear regression analysis. Using the sensitized erythrocytes there is no need to pre-absorb the serum samples to remove antibody cross-reacting with heterologous erythrocytes. Additionally it is unnecessary to pre-treat the serum samples to remove non-specific lipoprotein inhibitors.

Numerous modifications and variations of the abovedescribed invention will occur to those skilled in the art. For example, the antigen may be employed to sensitize immunologically inert particles of varying types well known in the art as useful in antigen-antibody detection schemes. In this regard, sensitized particles may be used in the detection of antibody by agglutination techniques, by radioimmunoassay techniques, by fluorescent techniques, and by enzyme immunoassay techniques. Additionally, particles such as erythrocytes and liposomes may be sensitized to provide an assay based on complement-mediated lysis.

What is claimed is:

1. A process for producing a soluble rubella antigen, said process comprising, in sequence:

(a) subjecting growth media of a tissue culture of rubella virus infected cells to chromatographic separation through a column consisting of a solid phase to which IgG, derived from human serum known to contain antibodies reactive with rubella antigens, has been convalently coupled;

(b) eluting from said column the rubella antigen materials bound to the IgG therein with a buffer having a pH of about 12;

(c) neutralizing the rubella antigen materials to a pH of about 8;

(d) subjecting the separated eluted rubella antigen materials to gel permeation chromatography to achieve material separation on the basis of molecular size;

(e) collecting the fractions containing said materials having a molecular weight of about 40,000 to about 60,000 daltons;

(f) isolating rubella antigen from said sized, separated eluted materials on the basis of relative reverse passive hemagglutination activity.

2. The process of claim 1 wherein, in step (a), the solid phase consists of agarose beads.

* * * * *